United States Patent
Cho et al.

(10) Patent No.: US 8,118,753 B2
(45) Date of Patent: Feb. 21, 2012

(54) BARB-WIRED MICRO NEEDLE MADE OF SINGLE CRYSTALLINE SILICON AND BIOPSY METHOD AND MEDICINE INJECTING METHOD USING THE SAME

(75) Inventors: Dong-il Cho, Seoul (KR); Seung Joon Paik, Seoul (KR); Jung Min Lim, Anyang-si (KR); Ah Ra Lee, Daegu (KR); Sang Won Byun, Seoul (KR); Kyo-In Koo, Kyunggi-do (KR)

(73) Assignee: Seoul National University Industry Foundation, Seoul (KR)

( * ) Notice: Subject to any disclaimer, the term of this patent is extended or adjusted under 35 U.S.C. 154(b) by 1016 days.

(21) Appl. No.: 12/069,592

(22) Filed: Feb. 12, 2008

(65) Prior Publication Data
US 2008/0208076 A1   Aug. 28, 2008

(51) Int. Cl.
*A61B 10/00* (2006.01)
*A61M 5/32* (2006.01)
(52) U.S. Cl. .................. 600/562; 600/564; 604/272
(58) Field of Classification Search .............. 604/22, 604/117, 164.01, 164.02, 164.12, 167.01, 604/183, 191, 171, 272–274, 43, 264, 46; 600/562, 564, 567, 570, 583; 606/20, 41, 606/424
See application file for complete search history.

(56) References Cited

U.S. PATENT DOCUMENTS

| 5,928,161 | A | 7/1999 | Krulevitch et al. |
| 6,132,755 | A * | 10/2000 | Eicher et al. ................ 424/427 |
| 6,638,249 | B1 | 10/2003 | Lal et al. ..................... 604/151 |
| 6,986,748 | B2 * | 1/2006 | McAlister et al. ........... 600/564 |
| 2004/0176732 | A1 * | 9/2004 | Frazier et al. ................ 604/345 |

FOREIGN PATENT DOCUMENTS

| JP | 2001-170059 | 6/2001 |
| KR | 2002-81743 | 10/2002 |
| KR | 1020040034175 A | 4/2004 |

* cited by examiner

*Primary Examiner* — Matthew F Desanto
(74) *Attorney, Agent, or Firm* — Head, Johnson & Kachigian, P.C.

(57) ABSTRACT

Disclosed are a barb-wired single crystalline silicon micro needle and a biopsy method and a medicine injecting method using the same. The micro needle comprises a main body part, at least one extension part formed on a side surface of the main body part, and a protrusion part protruded from both side surfaces of the extension part. A medicine storage is formed on a surface of the main body part. A fluid passage is formed in the extension part and the main body part. It is easy to pick the tissue sample with the protrusion part just by inserting and extracting the extension part of the micro needle into and from the tissue for a biopsy. Therefore, the biopsy procedures can be simplified. In addition, the medicine in the storage can be injected into the tissue via the fluid passage.

19 Claims, 15 Drawing Sheets

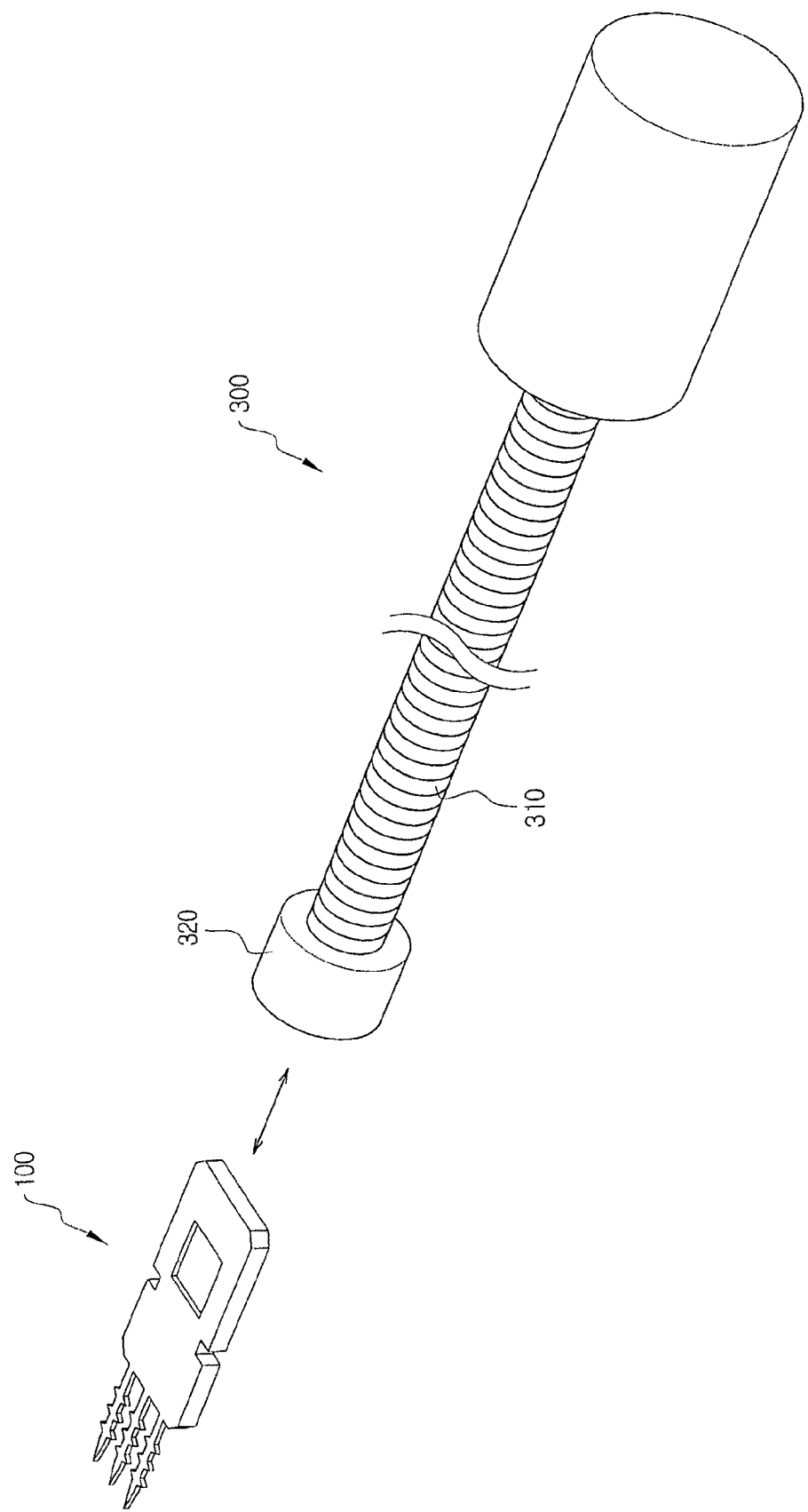

BARB-WIRED MICRO NEEDLE MADE OF SINGLE CRYSTALLINE SILICON AND BIOPSY METHOD AND MEDICINE INJECTING METHOD USING THE SAME

BACKGROUND OF THE INVENTION

1. Field of the Invention

The present invention relates to a micro needle made of single crystalline silicon, and more particularly to a barb-wired micro needle made of single crystalline silicon, capable of easily picking a tissue sample from a living body and adapted to inject a medicine into a lesion region of the tissue, and a biopsy method, and a medicine injecting method using the same.

2. Description of the Prior Art

In general, a pathological examination picking a sample of a living tissue from a patient so as to diagnose the patient's disease is a very important process to diagnose and treat the disease.

However, according to the prior art, since the tissue sample is picked from the patient using a biopsy device having a relatively big size, it is required a large quantity of reagents to analyze the picked tissue. In addition, the patient should endure pain and risk resulting from the medical treatment picking the tissue sample.

For solving the above problems, there are suggested micro biopsy/precision cutting devices made by applying a micro machining process and a precision process. The devices are disclosed in, for example, U.S. Pat. No. 5,928,161 (Krulevitch, et al.) entitled "Microbiopsy/Precision Cutting Devices."

However, according to the microbiopsy/precision cutting device, the biopsy procedures are very complex, and thus a skillful operator is required. In addition, since only a function of picking the tissue sample can be performed, an additional function of injecting a medicine into the tissue to treat a lesion region of the tissue cannot be performed.

A technology concerning transcorneal drug-release system and a micropin is disclosed in U.S. Pat. No. 6,132,755. Said transcorneal drug-release system and micropin are devices for injecting the drug into the skin, manufactured by sintering in a mould (col. 4 lines 12-15). The device is attached or fixed onto the skin like plaster or a wristwatch and cannot be inserted into the body. Therefore, said transcorneal drug-release system only injects drug into the skin and make the drug penetrate the Stratum corneum. Said transcorneal drug-release system is unable to pick tissue of an organ in the body or inject drug into a specific organ in the body.

SUMMARY OF THE INVENTION

Accordingly, the present invention has been made to solve the above-mentioned problems occurring in the prior art. The object of the present invention is to manufacture a micro needle as a biopsy device using a silicon micromachining process to miniaturize the micro needle, thereby performing a micro biopsy for a target tissue and minimizing an invasion of the biopsy device for a patient.

Another object of the invention is to pick a sample of a tissue through a simple process of inserting and extracting a micro needle into and from a target tissue, thereby simplifying biopsy procedures.

Still another object of the invention is to inject a medicine into a living tissue through a fluid passage in a micro needle, thereby treating a lesion region of the tissue.

In order to accomplish the objects, there is provided a barb-wired micro needle made of single crystalline silicon comprising a main body part including a medicine storage formed on a portion of one surface thereof and having a recess shape for storing the medicine and a fluid passage formed therein to communicate with the medicine storage and made of single crystalline silicon; an extension part integratedly extending from a side surface of the main body part, formed with the fluid passage therein and inserted into a biopsy tissue; and a protrusion part integratedly protruding from a side surface of the extension part and picking the biopsy tissue.

According to an embodiment of the invention, one or more protrusion part may be formed on both side surfaces or one surface of the extension part, and may be formed into one or more shape of a wing, a semicircle, a quadrangle and a triangle.

According to the invention, the wing-shaped protrusion part may comprise a protrusion part inclined in a forward or reverse direction for a longitudinal direction of the extension part toward a leading portion of the extension part. In addition, the wing-shaped protrusion part may comprise both a protrusion part inclined in a forward direction for a longitudinal direction of the extension part toward a leading portion of the extension part and a protrusion part inclined in a reverse direction for a longitudinal direction of the extension part toward a leading portion of the extension part.

The protrusion part may have a width of approximately 5 μm~5 mm, a space of approximately 5 μm~5 mm, and a height of approximately 5 μm~5 mm. Preferably, the protrusion part may have a width of approximately 50 μm~1 mm, a space of approximately 50 μm~1 mm, and a height of approximately 50 μm~1 mm.

According to the invention, two or more extension parts may be formed on the main body part. The extension parts may have a length of approximately 1.5 mm~15 mm and be formed apart from each other at an interval of approximately 5 μm~30 mm. Preferably, the extension part may have a length of approximately 2 mm~10 mm and be formed at an interval of approximately 100 μm~5 mm.

In order to achieve the above objects, there is provided a biopsy method using the barb-wired micro needle made of single crystalline silicon comprising steps of inserting the extension part of the micro needle into a desired tissue; separating the extension part from the tissue; and picking a sample of the tissue by the protrusion part of the extension part according to the separation of the extension part.

According to a preferred embodiment of the invention, the sample may be anchored to the extension part or between the extension parts.

In order to accomplish the above objects, there is provided a medicine injecting method using the barb-wired micro needle made of single crystalline silicon comprising steps of inserting the extension of the micro needle into a living tissue and injecting a medicine stored in the medicine storage via a fluid passage of the extension part.

In addition, in order to achieve the above objects, there is provided a medicine injecting method using the barb-wired micro needle made of single crystalline silicon comprising steps of inserting the extension of the micro needle into a living tissue having a lesion, and injecting a lesion-treating medicine or treatment-expediting medicine in the medicine storage into the tissue via a fluid passage of the extension part.

BRIEF DESCRIPTION OF THE DRAWINGS

The above and other objects, features and advantages of the present invention will be more apparent from the following detailed description taken in conjunction with the accompanying drawings, in which:

FIG. 5A illustrates an example of attaching a micro needle to a medical device.

DETAILED DESCRIPTION OF THE PREFERRED EMBODIMENTS

Hereinafter, preferred embodiments of the present invention will be described with reference to the accompanying drawings. In the following description of the present invention, a detailed description of known functions and configurations incorporated herein will be omitted when it may make the subject matter of the present invention rather unclear.

Figure 1A:
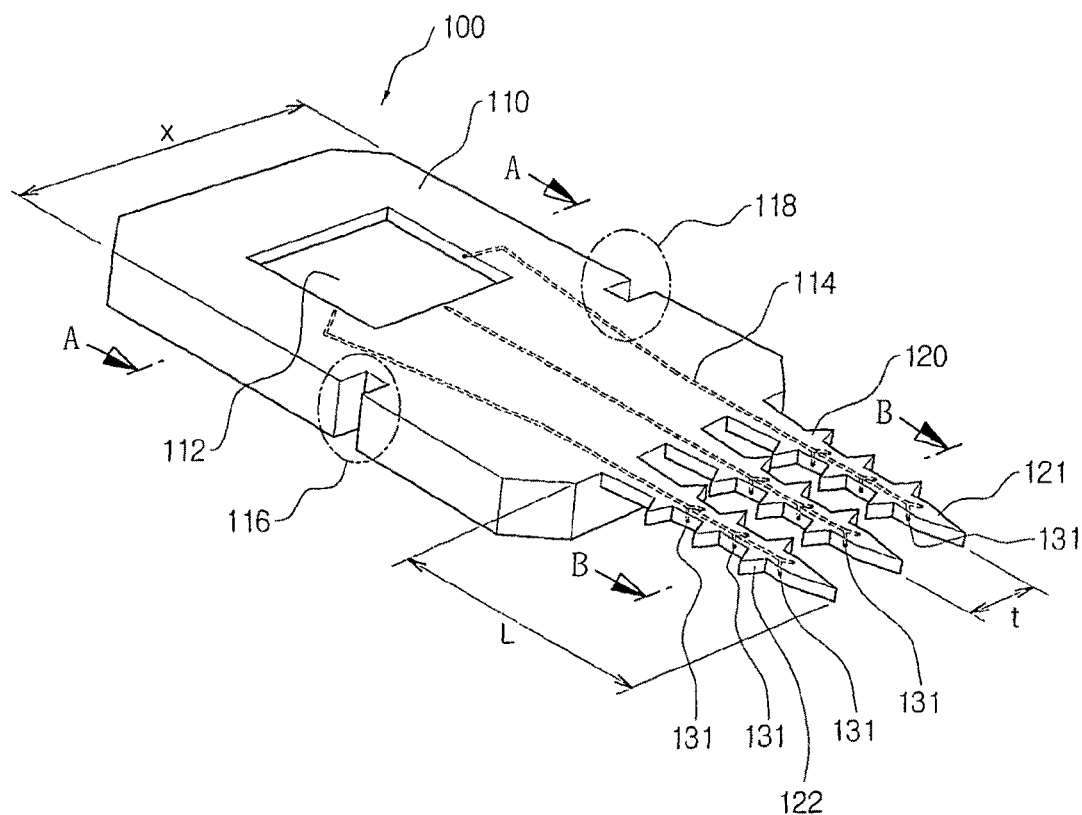
FIGS. 1A and 1B are a perspective view and a side view of a barb-wired micro needle made of single crystalline silicon according to an embodiment of the invention, respectively.
Figure 1B:
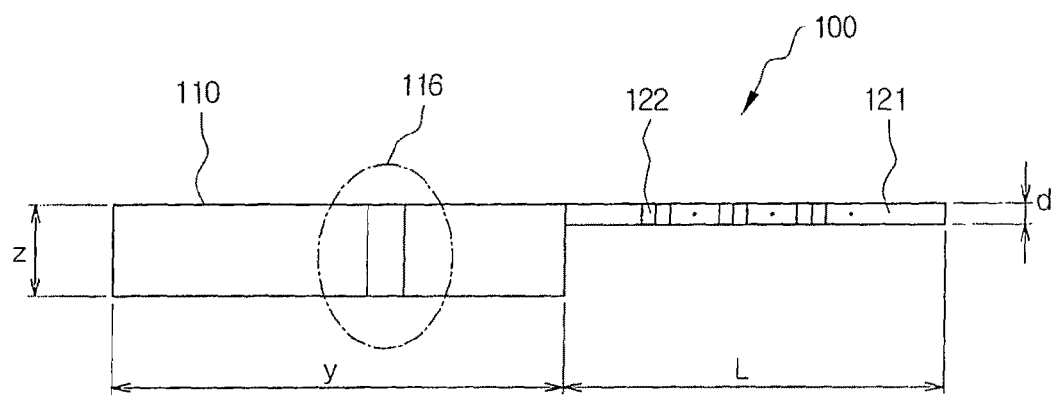

FIG. 1A is a schematic view showing a barb-wired single crystalline silicon micro needle according to an embodiment of the invention. FIG. 1B is a side view of a micro needle according to the embodiment of the invention.

Referring to FIGS. 1A and 1B, the micro needle 100 according to an embodiment of the invention comprises a main body part 110, an extension part 120 and a protrusion part 122. The micro needle may be embodied in one body integrated with the main body part 110, the extension part 120 and the protrusion part 130 and made of single crystalline silicon.

The main body part 110 is made of single crystalline silicon, and a surface of the main body part 110, for example, a portion of an upper surface thereof is provided with a medicine storage 112 having a recess shape for storing medicine (not shown). Here, a medicine may be introduced into the medicine storage 112, and then a cover (not shown) made of plastic (e.g., PDMS, polydimethylsiloxane) may cover the medicine storage 112. The cover and the main body part 110 may be bonded through $O_2$ plasma process. Alternatively, the cover may previously cover the medicine storage 112 by bonding cover and the main body part 110 when manufacturing the micro needle of the invention, and then a medicine may be injected into the medicine storage 112 through the cover by a syringe when using the micro needle.

The main body part 110 comprises a connection means that is structured to easily connect with a mount device, for example, a medical device such as an endoscope, capsule-type endoscope, catheter, tweezers or a pincette. For instance, the micro needle 100 according to the invention can be easily connected and separated to and from an existing medical device (e.g., endoscope) just by forming a connection means, such as a recess 116, 118 in the main body 110 through which the main body part 110 can be inserted into the medical device.

Figure 2:
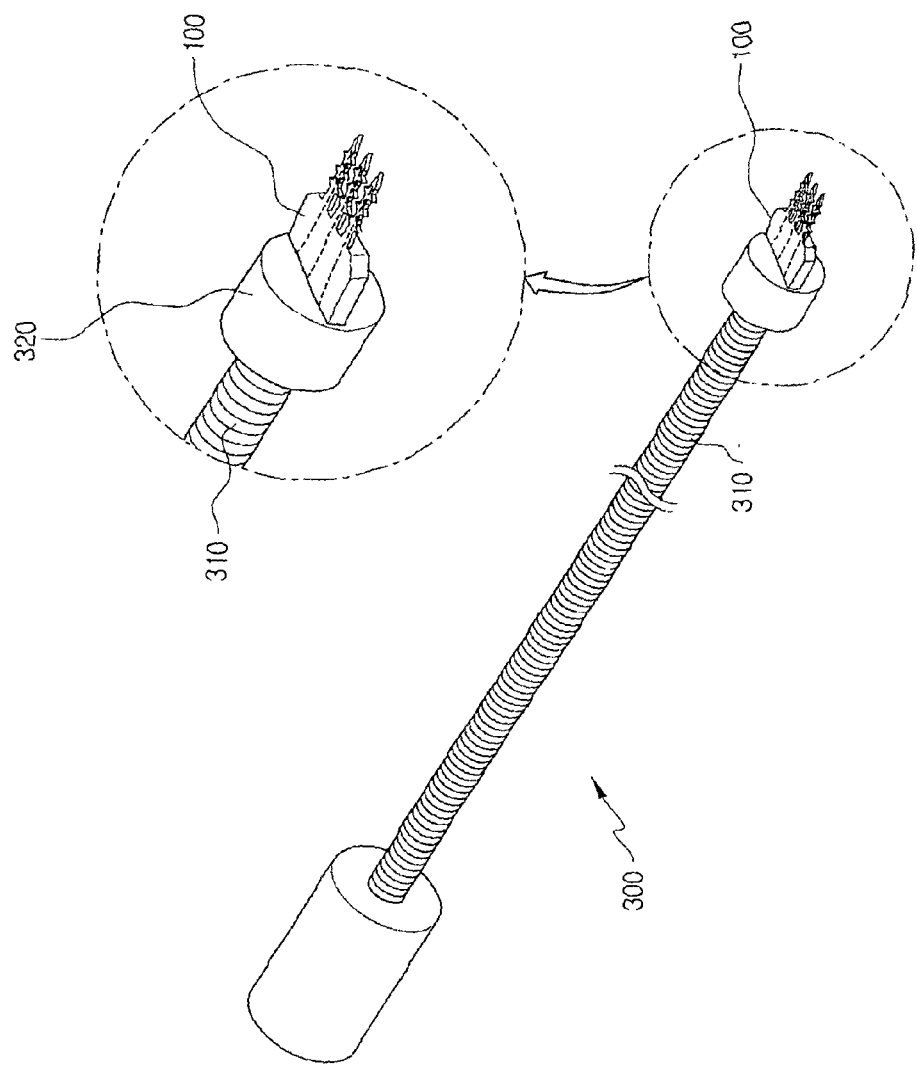
FIG. 2 illustrates an example of a micro needle attached to a medical device.

FIG. 2 illustrates an example of the way in which a micro needle 100 according to the invention is attached to a medical device 300 such as a catheter. A micro needle 100 according to the invention is attached to the end part 320 of the wire 310 of said medical device 300, and the wire 310 of said medical device 300 is inserted into the body. For example, it is inserted into the body by piercing the skin or inserted into the esophagus or the intestine like an endoscope and close to the organ (e.g., stomach, liver, intestine, etc.) in the body.

Afterwards, said micro needle 100 attached to the end part 320 of said wire 310 is inserted into the organ to be examined, and when the wire 310 of said medical device 300 is taken out of the body, the tissue picked by said micro needle 100 is also taken out of the body. In sum, the tissue of an organ in the body can be picked by inserting a micro needle 100 into the body along with the wire 310 of a medical device 300 and taking them out of the body.

Referring again to FIGS. 1A and 1B, the extension part 120 is made of single crystalline silicon and integratedly connected to a side surface of the main body part 110. The extension part 120 is inserted into a living tissue and has a thickness smaller than that(z) of the main body part 110. A leading portion 121 of the extension part 120 is shaped to be easily inserted into the living tissue. For example, the leading portion is shaped into a pointed form.

A fluid passage 114 is formed within the main body part 110 and the extension part 120 to communicate with the medicine storage 112. The fluid passage 114 is extended to a side surface of the extension part 120. Plural outflow ports 131 of the fluid passage 114 are formed on a side surface or both side surfaces of each extension part.

It can be determined that a length (L) of the extension part 120 is within a range of about 10 µm~10 mm, and a space (t) between the extension parts 120 is within a range of about 5 µm~5 mm. Although only three extension parts 120 are shown in FIG. 1 for convenient explanations, it should be noted that two or more extension part 120 can be provided.

Figure 3:
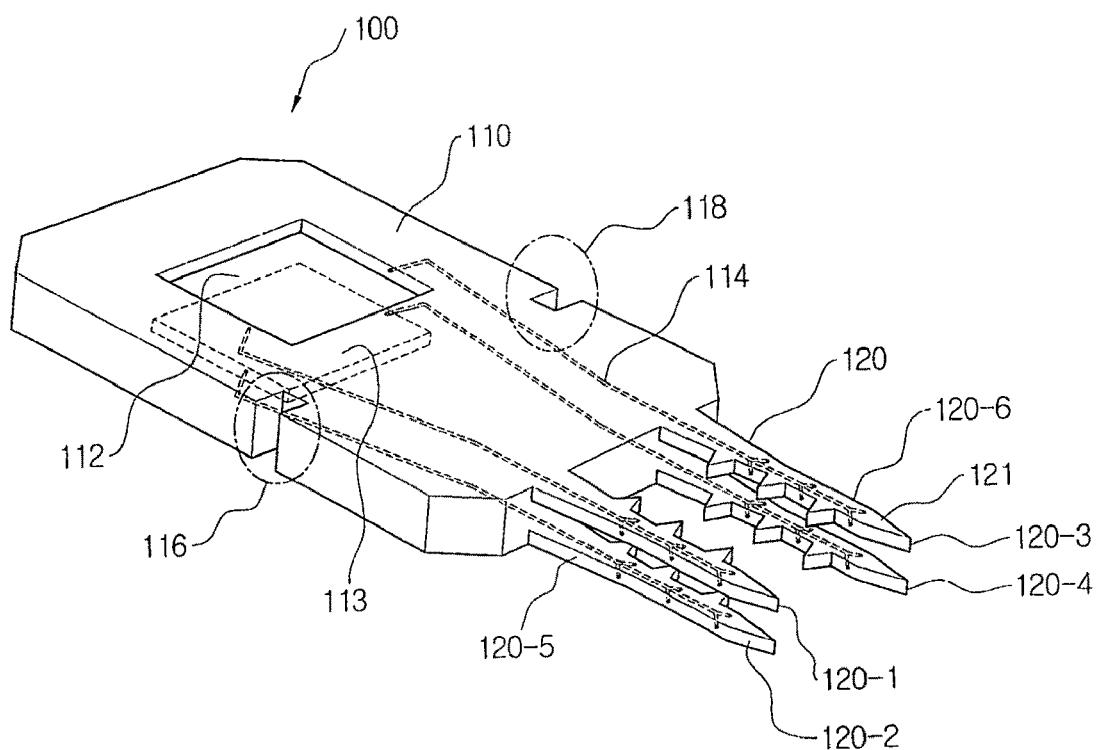
FIG. 3 illustrates a micro needle according to another embodiment of the invention.

For example, two extension parts 120 are respectively formed by extending from the left part (120-1, 120-2) and right part (120-3, 120-4) of the main body part 110. In addition, the extension parts may be provided to the upper and/or lower parts of the one side of the main body part 110. The number of the extension parts provided to the upper or lower parts of the one side of the main body part 110 may be from 1 to 10. FIG. 3 illustrates an example of a micro needle wherein left part extension parts(120-1, 120-2) and right part extension parts(120-3, 120-4) are formed by extending from the upper part(120-1, 120-3) and the lower part(120-2, 120-4) of the main body part 110. Here, another medicine storage 113 may be further provided on the bottom surface of the main body part 110. The medicine storage 113 is connected with the extension parts(120-2, 120-4) which are extended from the lower part of the main body part 110.

In addition, the protrusion part 122 is made of single crystalline silicon and integratedly protruded from a side surface of the extension part 120. One or more protrusion part 122 may be provided at an interval to the side surface of the extension part 120. The protrusion part 122 serves to induce a picking of a tissue sample from the living tissue and to anchor the picked tissue when performing a biopsy using the extension part 120.

Figure 4A:
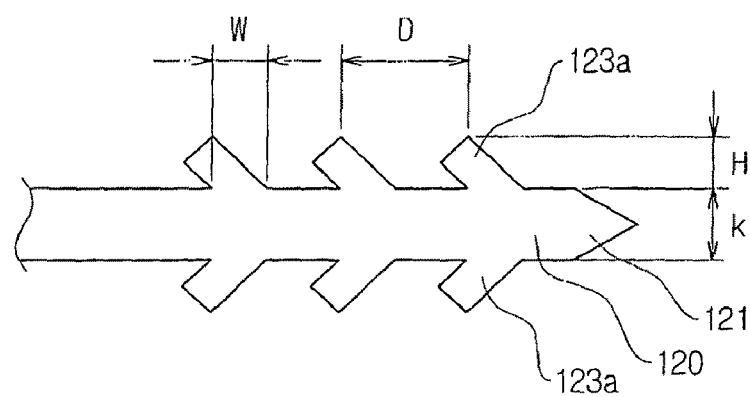
FIGS. 4A to 4F are plan views illustrating various shapes of a protrusion part applied to an extension part of a micro needle according to an embodiment of the invention.

The protrusion part 122 may be formed into various shapes as shown in FIGS. 4A to 4F. Specifically, a protrusion part 123a may have a wing shape inclined in a forward direction for a longitudinal direction of the extension part 120 toward the leading portion 121 of the extension part 120, and may be integratedly protruded from both side surfaces of the extension part 120, as shown in FIG. 4A. It can be determined that a width (W) of the protrusion part 123a, a space (D) between the protrusion parts, and a height (H) of the protrusion part are within a range of about 5 μm~5 mm, respectively.

It is preferred that said protrusion part 130 be formed on the side surfaces of said extension part 120, which are opposite to each other as shown in FIG. 3. For example, a protrusion part 130 is not formed on the outer side surfaces of the extension part 120 of the micro needle shown in FIG. 3. It is also possible that protrusions parts 122 are formed on both side surfaces of the extension part 120 which are formed at the center of the main body 110 as shown in FIG. 1A.

Figure 4B:
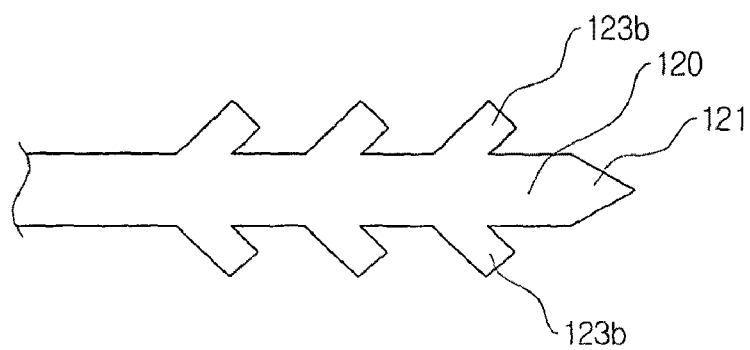

In addition, a protrusion part 123b may have a wing shape inclined in a reverse direction for a longitudinal direction of the extension part 120 toward the leading portion 121, and may be integratedly protruded from both side surfaces of the extension part 120, as shown in FIG. 4B.

Figure 4C:
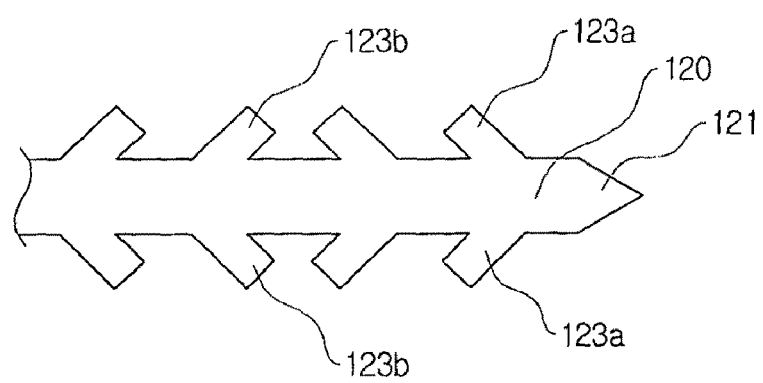

Additionally, the protrusion part 123b may be provided to the side surfaces of the extension part 120 together with the protrusion part 123a, as shown in FIG. 4C.

In case of that only the protrusion parts 123a are provided, it is possible to pick a large quantity of tissue sample from a tissue for the biopsy when the extension part 120 inserted into the tissue is separated from the tissue. In case of that only the wing-shaped protrusion parts 123b are provided, it is possible to pick a large quantity of tissue sample from a tissue for the biopsy when the extension part 120 is inserted into the tissue. In case of that the protrusion parts 123a, 123b are together provided, it is possible to pick a large quantity of tissue sample from a tissue for the biopsy both when the extension part 120 is inserted into the living tissue and when the extension part 120 is separated from the living tissue.

Figure 4D:
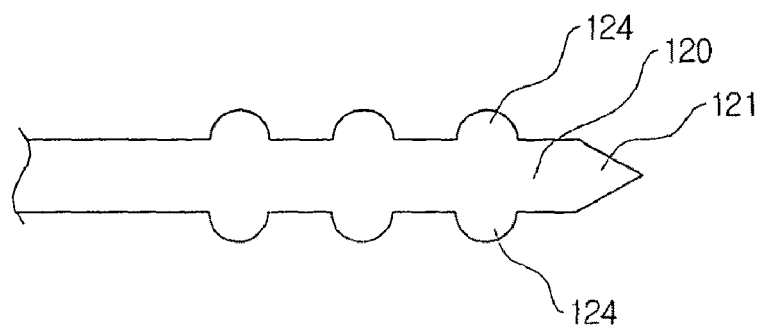
Figure 4E:
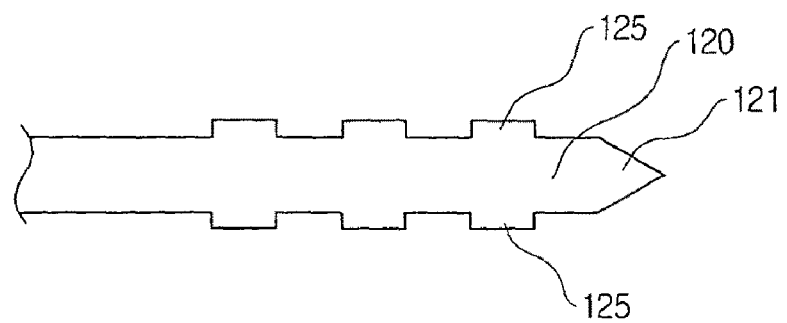
Figure 4F:
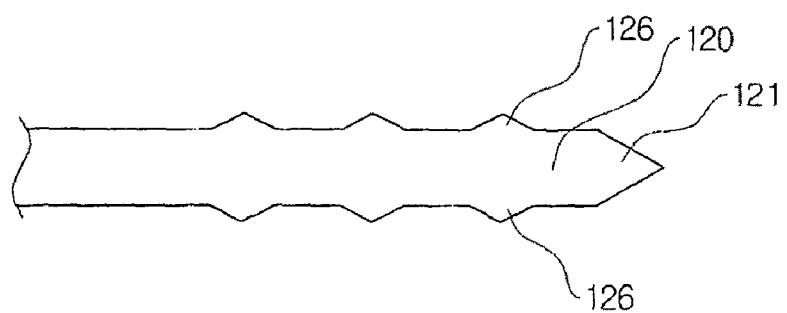

In addition, a protrusion part 124 may have a curved shape, for example, a semicircular shape as shown in FIG. 4D, and may be integratedly formed on both side surfaces of the extension part 120. A protrusion part 125 may have a quadrangle shape, for example, a rectangular shape as shown in FIG. 4E, and may be integratedly protruded from both side surfaces of the extension part 120. A protrusion part 126 may have a triangular shape as shown in FIG. 4F, and may be integratedly protruded from both side surfaces of the extension part 120.

Additionally, similarly to the protrusion part shown in FIG. 4A, it can be determined that a width, a space and a height of the protrusion parts 123a, 123b, 124, 125, 126 shown in FIGS. 4B to 4F are within a range of about 5 μm~5 mm.

Although not shown for convenient explanations, at least two shapes of the semicircular, quadrangle and triangular protrusion parts 124, 125, 126 may be together provided to the both side surfaces of the extension part 120, similarly to the embodiment shown in FIG. 4C. Of course, besides the wing-shaped, semicircular, quadrangle and triangular protrusion parts, protrusion parts having various shapes may be formed on the both side surfaces of the extension part 120. As mentioned above, it is not necessarily to form the protrusion part on the both side surfaces of the extension part 120, and the protrusion part may be provided to only one side surface of the extension part 120.

In the mean time, considering a characteristic of a device being inserted into a living body, a size thereof is preferably limited within a predetermined range. From this point of view, it is preferred that a length (L in FIG. 1B) of the extension part 120 is within a range of 1.5 mm~15 mm (more preferably, 2 mm~10 mm), and an interval (t in FIG. 1A) between the extension parts 120 is within a range of 5 μm(micrometer)~30 mm (more preferably, 100 μm~5 mm). Further, it is preferred that the width (k in FIG. 4A) of said extension part 120 is within a range of 10 μm~10 mm (more preferably, 100 μm~1 mm). Further, it is also preferred that the thickness (d in FIG. 2B) of said extension part 120 is within a range of 10 μm~10 mm (more preferably, 100 μm~1 mm).

Further, the main body part 110 of a micro needle 100 according to the invention is also inserted into the body by a medical device, and therefore, it is preferable that the size of said main body part 110 be limited to a certain range. For instance, it is preferred that the width (x in FIG. 1A) be within the range of 100 μm~50 mm (more preferably 1 mm~5 mm). It is preferred that the length (y in FIG. 1B) of said main body part 110 also be limited to 100 μm~50 mm (more preferably 500 μm~5 mm). It is preferred that the thickness (z in FIG. 1B) of said main body part 110 be limited to 100 μm~10 mm (more preferably 200 μm~2 mm).

Figure 5B:
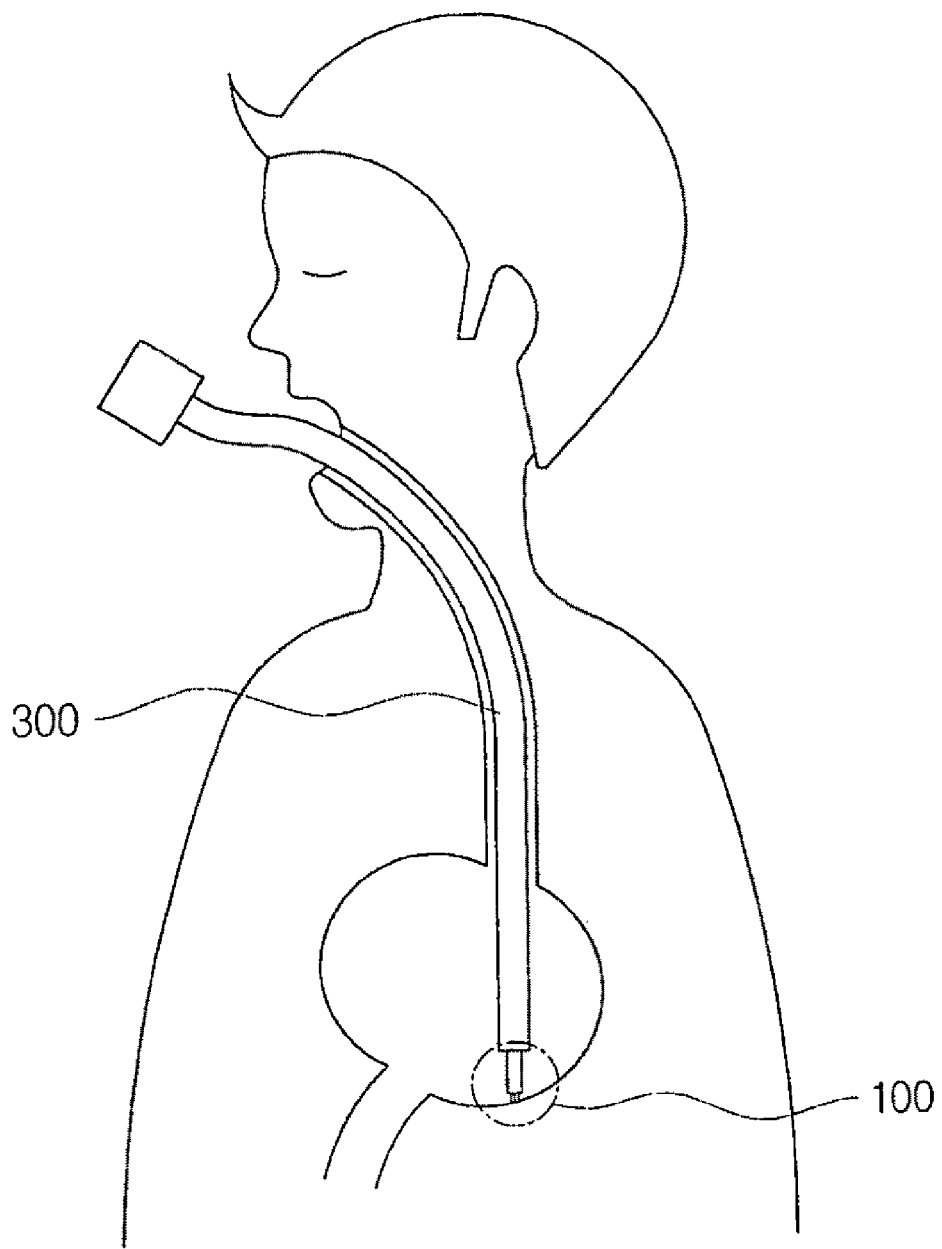
FIGS. 5B to 5D are exemplary views showing an extension part of a micro needle according to an embodiment of the invention inserted into a tissue for a biopsy.
Figure 5C:
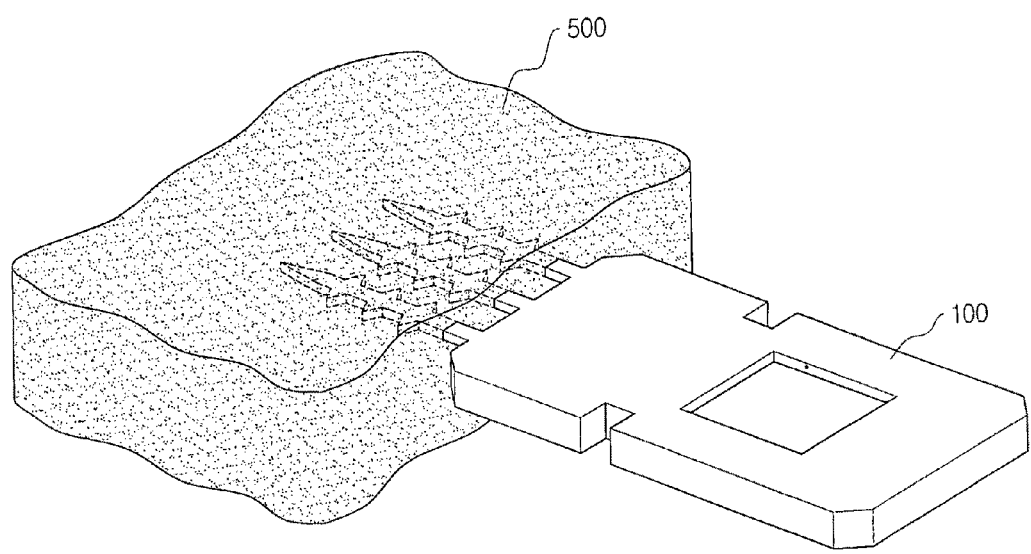
Figure 5D:
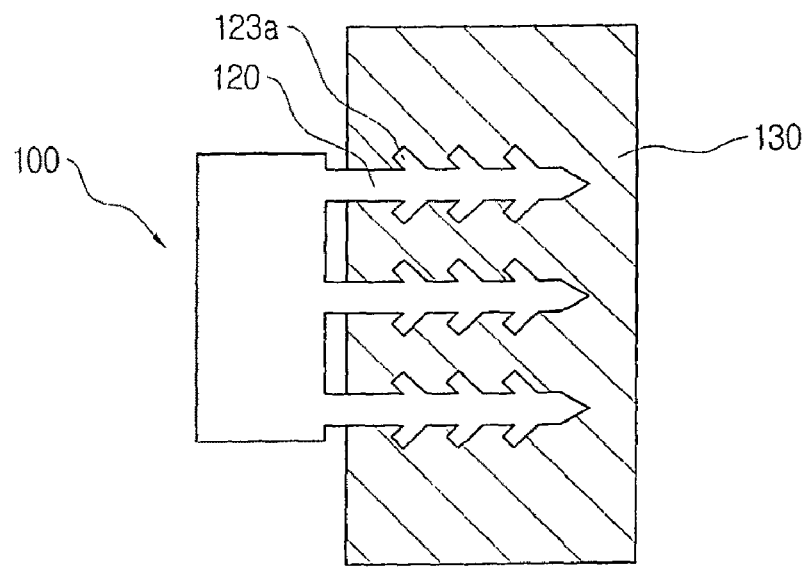

Hereinafter, biopsy procedures using the micro needle 100 having the above-described structure will be explained. As shown in FIG. 5A, a micro needle 100 according to the invention is attached to the end part 320 of a wire 310 of a medical device 300 such as an endoscope. Then, a medical device 300 on which the micro needle according to the invention is attached is inserted into a body to pick the tissue of an organ in the body as shown in FIG. 5B. Then, as shown in FIGS. 5C and 5D, the extension part 120 of the micro needle 100 attached to the medical device is inserted into a tissue region 500 where the pathological examination is to be conducted for a biopsy so as to pick a sample or cell from the tissue 500 of a patient's organ.

Figure 5E:
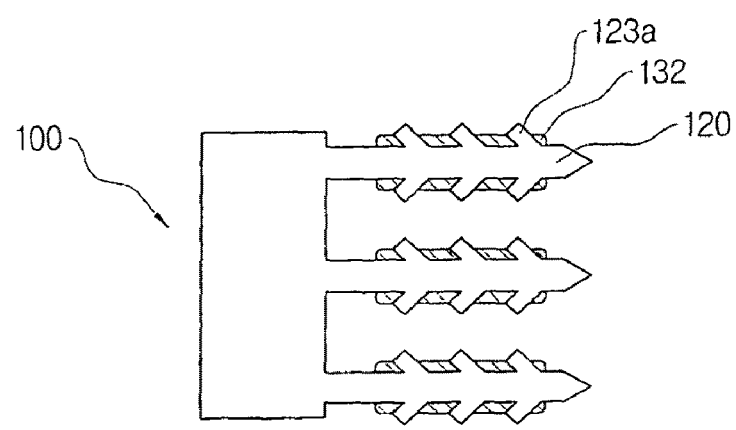
FIG. 5E is an exemplary view showing protrusion parts of an extension part of a micro needle according to an embodiment of the invention, to which a tissue sample is picked and anchored.
Figure 5F:
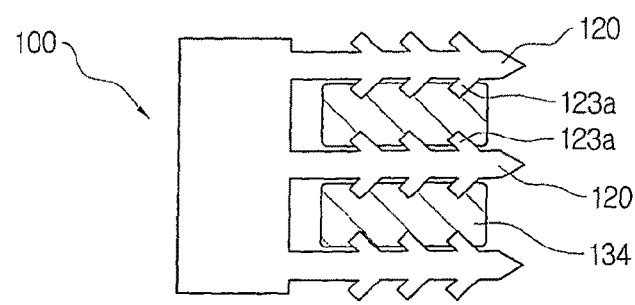
FIG. 5F is an exemplary view showing extension parts of a micro needle according to an embodiment of the invention, between which a tissue sample is picked and anchored.

Under such state, as shown in FIGS. 5E and 5F, when the extension part 120 is separated from the tissue 130, samples 132, 134 of the tissue 130 are picked by the protrusion part 123a of the extension part 120. At this time, the sample 132 may be anchored to the extension part 120 by the protrusion part 123a as shown in FIG. 5E, or the sample 134 may be anchored between the extension parts 120 by the protrusion part 123a as shown in FIG. 5F.

Accordingly, since the micro needle 100 of the invention can be miniaturized through a silicon micromachining process, it is possible to miniaturize the biopsy device, to perform a micro biopsy for the tissue and to minimize an invasion of the biopsy device for the patient.

In addition, since it is possible to easily pick a sample of the tissue 130 just by inserting and extracting the extension part 120 of the micro needle 100 into and from the tissue 130, biopsy procedures can be simplified.

Figure 6:
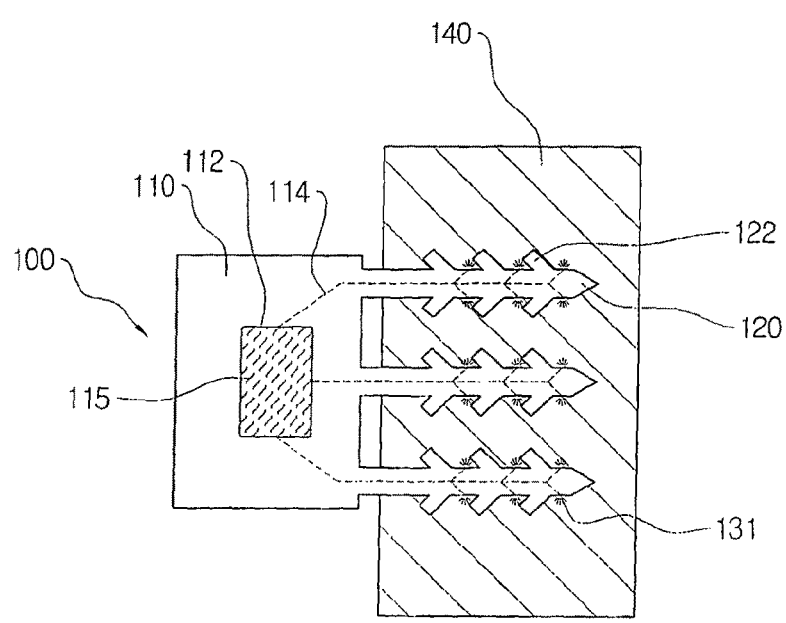
FIG. 6 shows an exemplary procedure of injecting a medicine into a tissue via an extension part of a micro needle according to an embodiment of the invention.

Further, according to the micro needle 100 of the invention, as shown in FIG. 6, under such state that the extension part 120 having the wing shaped protrusion part 123a as shown in FIG. 4A is inserted into a tissue 140, a medicine 115 stored in the medicine storage 112 of the main body part 110 can be injected into the tissue 140 via the fluid passage 114 and the outflow ports 131 formed in the main body part 110 and the extension part 120 by a known apparatus (not shown) such as a micro pump disclosed in Korean Unexamined Patent Publication No. 2002-81743. Accordingly, it is possible to treat a lesion of the tissue 140 or expedite a lesion treatment by injecting a medicine suitable for the treatment into the tissue 140. Further, when performing the biopsy as shown in FIGS. 5B to 5F, it is possible to promote a cell or sample picking of the tissue 140 by injecting the medicine suitable for the picking into the tissue 140.

The micro needle 100 can be used as an individual device for the biopsy and the lesion treatment. Further, when it is mounted together with a known suction device (not shown), the micro needle can pick body fluids from a patient's organ, for example, a digestive organ, into the medicine storage 112. In addition, it is possible to use the micro needle 100 together with a medical device such as an endoscope for the biopsy and the treatment.

Hereinafter, a method of manufacturing the micro needle 100 will be explained with reference to FIGS. 7A to 7F. For convenient explanations, a section of the main body part 110 taken along a line A-A in FIG. 1A will be described in conjunction with a section of the extension part 120 taken along a line B-B.

Referring to FIG. 5A, an insulation film 3 as an etching mask layer of a single crystalline silicon substrate 1 is formed on one surface of the substrate 1, for example, an upper surface in which the medicine storage 112 shown in FIG. 1 will be formed. Specifically, a silicon oxide film (not shown) is grown on an overall upper surface of the silicon substrate 1 by a thermal oxidation method, and then a low stress silicon nitride film (not shown) is deposited on the silicon oxide film by, for example, a low pressure chemical vapor deposition method, thereby forming the insulation film 3 consisting of a stacked structure of the silicon oxide film and the silicon nitride film. The silicon oxide film serves as both a thermal barrier layer and an electric insulating layer.

After that, a fluid passage forming area for the fluid passage 114 shown in FIG. 1A is defined on portions of a main body part forming area 10 and an extension part forming area 20 of the silicon substrate 1 using a photographing process. In other words, a photoresist film (not shown) as an etching mask layer for the insulation film 3 is coated on the insulation film 3. Then, the photoresist film on the fluid passage forming area is selectively removed until the insulation film 3 under the photoresist is exposed, thereby forming a pattern of the photoresist film exterior to the fluid passage forming area.

Then, the exposed portion of the insulation film 3 is etched using the pattern of the photoresist film as an etching mask layer until the silicon substrate 1 under the insulation film is exposed, thereby forming a pattern of the insulation film 3. Subsequently, the pattern of the photoresist film on the pattern of the insulation film 3 is completely removed.

Then, using the pattern of the insulation film 3 as the etching mask layer, the exposed portion of the silicon substrate 1 is anisotropically etched to a desired depth by an anisotropic etching process, for example, a chlorine-based plasma etching process or Bosch process, thereby forming a trench 41 in the fluid passage forming area. In the figure, the trench 41 is shown to be formed in only a portion of the extension part forming area 20. However, it is obvious that the trench is also formed in a portion of the main body part forming area 10 to communicate with the medicine storage 112 of FIG. 1A.

In the mean time, although it is explained based on that one extension part is formed in the extension part forming area 20 and one fluid passage 114 is formed in the extension part, it is obvious that one or more extension part may be formed in the extension part forming area 20 and one fluid passage 114 may be formed in each of the extension parts.

Figure 7A:
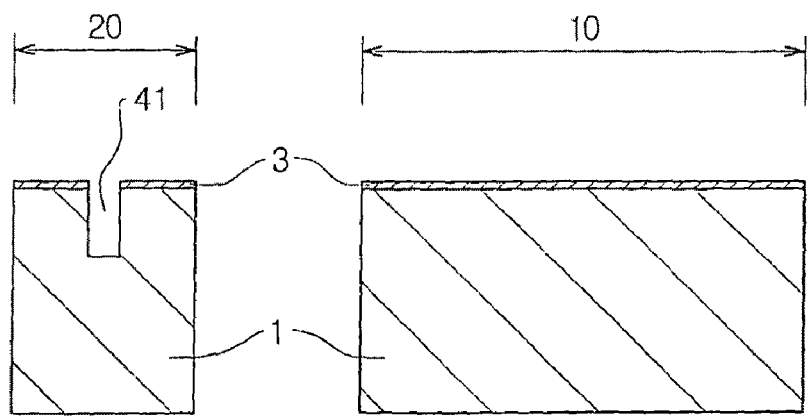
FIGS. 7A to 7F are sectional views illustrating a method of manufacturing a micro needle according to an embodiment of the invention.
Figure 7B:
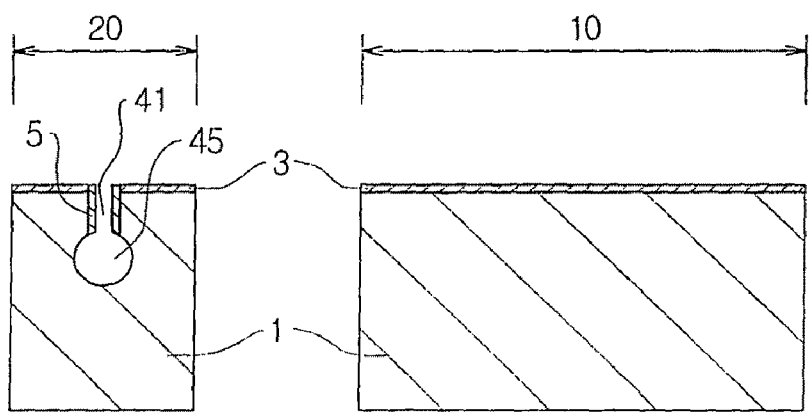

Referring to FIG. 7B, a protective film 5 which is an insulation film having a good step coverage is formed on a side of the trench 41. Specifically, for example, a silicon oxide film (not shown) and a silicon nitride film (not shown) having a good step coverage are sequentially deposited in the trench 41 and on the insulation film 3 exterior to the trench 41 by a low pressure chemical vapor deposition method. The reason is to prevent a side damage of the trench 41 due to the etching in a subsequent silicon substrate-etching step for forming the fluid passage 114 in FIG. 1A.

Subsequently, the protective film 5 is etched using the anisotropic etching process, for example, an etch back process until the silicon substrate 1 in a bottom portion of the trench 41 is exposed, and the protective film 5 exterior to the trench 41 is also etched, thereby leaving the protective film 5 on only the side of the trench 41 and exposing the pattern of the insulation film 3.

After that, the exposed silicon substrate 1 in the trench 41 is isotropically etched by an isotropic etching process, thereby forming a semicircular fluid passage 45 under the trench 41. At this time, any one of a dry etching process using $SF_6$ plasma and $XeF_2$ gas, etc. or a wet etching process using hydrofluoric acid/nitric acid/acetic acid, etc. may be used for the isotropic etching.

Figure 7C:
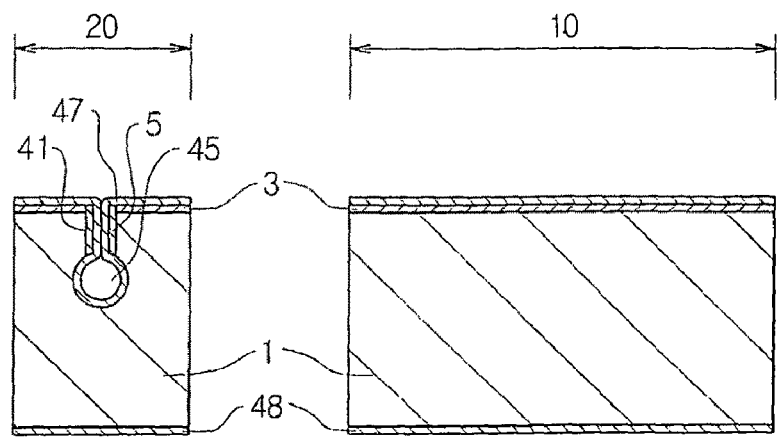

Referring to FIG. 7C, films of the same quality 47, 48 are simultaneously deposited on upper and lower surfaces of the silicon substrate 1 structured according to the above procedures in order to seal the trench 41 hermetically, thereby forming a complete fluid passage 45 in the extension part forming area 20 of the silicon substrate 1. At this time, although not shown, it is obvious that a complete fluid passage is also formed in the main body part forming area 10 of the silicon substrate 1.

Specifically, a film 47, for example, a polycrystalline silicon film, a silicon oxide film or a silicon nitride film is uniformly deposited on inner surfaces of the trench 41 and the fluid passage 45 by the low pressure chemical vapor deposition method. As a result of that, when the film 47 is gradually thickened from both opposing inner surfaces of the trench 41 toward a center of the trench 41, and then the films 47 on both inner surfaces are contact to each other, the trench 41 is hermetically sealed by the film 47, so that the fluid passage 45 is completed.

Accordingly, since the fluid passage 45 is formed in the bulk silicon substrate, there little occurs a transformation of the micro needle structure due to the stress of the thin film. This improves durability of the main body part and the fluid passage 45 of the micro needle.

In the mean time, the film 47 consists of a film capable of being deposited by the low pressure chemical vapor deposition method, for example, one or more of a polycrystalline silicon film, a silicon oxide film and a silicon nitride film. In addition, instead of using the low pressure chemical vapor deposition method for sealing the trench 41 hermetically, a coating process using a bio-compatible organic thin film such as a parylene thin film may be used. Additionally, separating from the process described in connection with FIG. 7B or 7C, when the silicon substrate 1 is heat-treated in a hydrogen atmosphere and a temperature of 1100° C. after the trench 41 is formed, the crystals are re-combined and thus an upper part of the trench 41 is hermetically sealed. The fluid passage 45 may be formed using such phenomenon.

After that, a planarization process for planarizing a surface of the silicon substrate 1 may be further performed to carry out a subsequent photographing process smoothly. However, when a width of the trench 41 is small, the planarization process may be not performed.

Figure 7D:
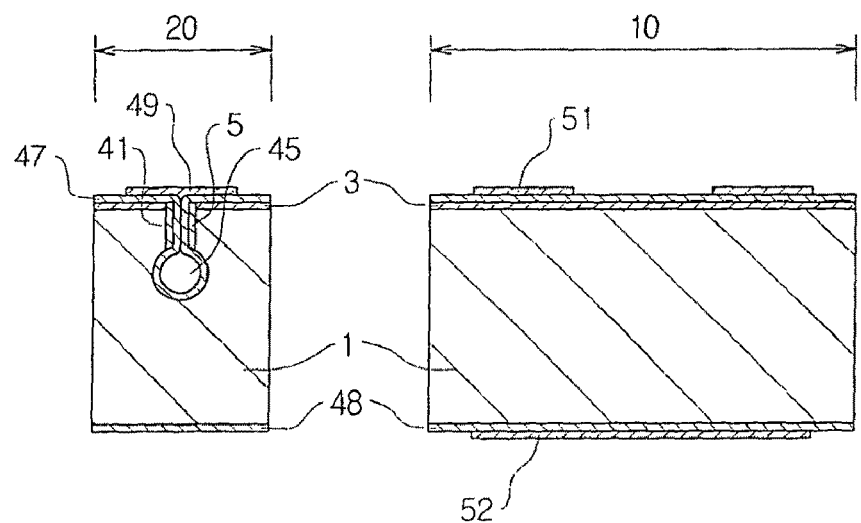

Referring to FIG. 7D, an insulation film, for example, a silicon oxide film or a silicon nitride film is deposited on the upper and lower surfaces of the silicon substrate 1. After that, using a photograph etching process, a pattern of an insulation film 49 for forming patterns of the extension part 120 and the protrusion part 122 shown in FIG. 1A is left on a portion of the upper surface of the silicon substrate 1 in the extension part forming area 20, and patterns of insulation films 51, 52 for forming a pattern of the medicine storage 112 shown in FIG. 1 are respectively left on portions of the upper and lower surfaces of the silicon substrate 1 in the main body part forming area 10.

It can be determined that a length (L) of the extension part 120 is within a range of about 1.5 mm~15 mm, and a space (t) of the extension parts 120 is within a range of about 5 μm~30 mm.

In addition, the protrusion part may be formed into various shapes as well as the shapes of the wing-shaped, semicircular, quadrangle and triangular protrusion parts 123a, 123b, 124, 125, 126 as shown in FIGS. 4A to 4F. The width (W), the space (D) and the height (H) of the protrusion parts 123a, 123b, 124, 125, 126 may be set to be within a range of about 5 μm~5 mm.

Figure 7E:
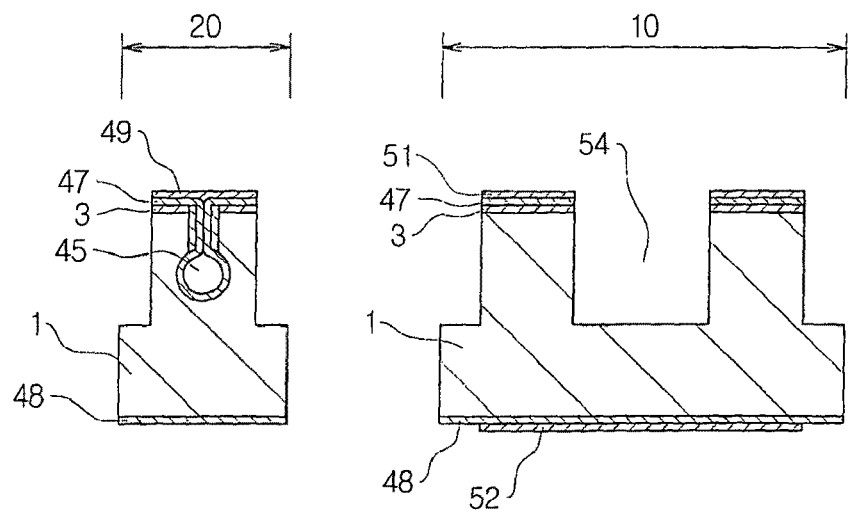

Referring to FIG. 7E, the films 47, 3 are etched using the patterns of the insulation films 49, 51 as the etching mask layer. Then, the silicon substrate 1 is anisotropically etched to a desired depth by the anisotropic etching process, for example, a reactive ion etching process, thereby defining a pattern of the main body part 110 shown in FIG. 1 on a portion of the main body part forming area 10 of the silicon substrate 1, forming a pattern of a recess portion 54 corresponding to the medicine storage 112, and forming patterns corresponding to the patterns of the extension part 120 and the protrusion part 122 shown in FIG. 1 on a portion of the extension part forming area 20 of the silicon substrate 1.

Since the etched depth of the silicon substrate 1 determines a depth of the medicine storage 112 and thicknesses of the extension part 120 and the protrusion part 122, it is preferred to determine the etched depth, considering a diameter of the fluid passage 45 and a depth of the trench 41.

Figure 7F:
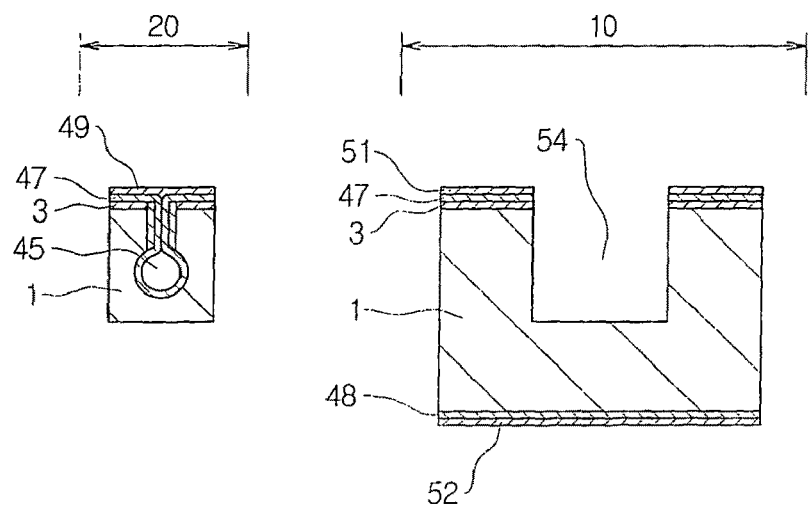

Referring to FIG. 7F, the film 48 is etched using the insulation film 52 on the lower surface of the silicon substrate 1 as the etching mask layer until the lower surface of the silicon substrate 1 under the film is exposed.

Figure 8:
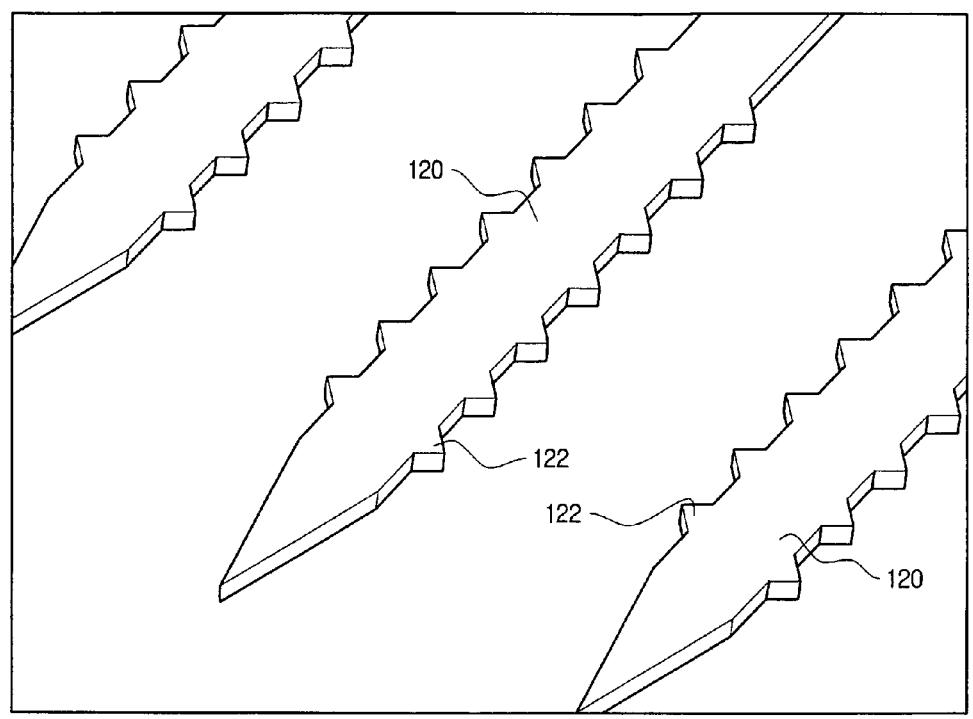
FIG. 8 is perspective view showing a structure of an extension part and a protrusion part of a micro needle according to an embodiment of the invention.

Subsequently, using the pattern of the insulation film 52 as the etching mask layer, the lower surface of the silicon substrate 1 is anisotropically etched to a desired thickness by the anisotropic etching process, for example, a reactive ion etching process, thereby completing the main body part 110, the extension part 120 and the protrusion part 122 of the micro needle 100 as shown in FIG. 1A. The completed structure of the extension part 120 and the protrusion part 122 is shown in FIG. 8.

The lower surface of the silicon substrate 1 may be etched by an isotropic etching process instead of the anisotropic etching process.

According to the invention, since the barb-wired single crystalline silicon micro needle is manufactured using a silicon micromachining process, the micro needle can be easily miniaturized. In addition, a reproducibility of the micro needle is superior and it is possible to improve the durability of the micro needle itself and the fluid passage.

In addition, since the micro needle can be easily miniaturized, it is possible to easily miniaturize the biopsy device, to perform a micro biopsy for the tissue and to minimize the invasion of the biopsy device for the patient.

Additionally, since the extension part of the micro needle is formed with the protrusion part, it is possible to easily pick the cell or sample of the tissue just by inserting and extracting the extension part into and from the tissue and thus to simplify the biopsy procedure.

Further, since the medicine can be injected into the tissue via the fluid passage in the micro needle, the micro needle can be used as an individual device capable of treating the lesion and expediting the treatment. In addition, it can be used together with a medical device such as an endoscope.

While the invention has been shown and described with reference to certain preferred embodiments thereof, it will be understood by those skilled in the art that various changes in form and details may be made therein without departing from the spirit and scope of the invention as defined by the appended claims.

What is claimed is:

1. A barb-wired micro needle monolithically formed from a single crystalline silicon comprising;
   a main body part capable of being insertion-mounted to a medical device and inserted into the body along with said medical device for picking a tissue sample from an organ in a body, the main body part including a medicine storage formed on a portion of one surface thereof and having a recess shape for storing medicine and a fluid passage formed therein to communicate with the medicine storage and made of single crystalline silicon;
   plural extension parts integrally extending from a side surface of the main body part, provided with the fluid passage therein and capable of being inserted into a biopsy tissue; and
   plural protrusion parts integrally protruding from a side surface or both side surface of the extension parts, and capable of picking the biopsy tissue,
   wherein plural outflow ports of the fluid passage are formed on both side surface of each of the extension parts for injecting medicine into an organ in a body.

2. The micro needle according to claim 1, wherein at least four extension parts are integrally extended from upper and lower parts, and left and right parts of one side of the main body part.

3. The micro needle according to claim 2, wherein at least an extension parts are further formed between the extension part from the left part and the extension part from the right part on the one side of the main body part.

4. The micro needle according to claim 3, wherein protrusion parts are formed on both side surface of the extension part which is formed between the extension part from the left part and the extension part from the right part on the one side of the main body part.

5. The micro needle according to claim 2, wherein the number of the extension parts respectively formed at the upper and lower parts of the one side of the main body is between 1 and 10.

6. The micro needle according to claim 1, wherein the protrusion part is formed into a shape of a wing.

7. The micro needle according to claim 6, wherein the wing-shaped protrusion part comprises a protrusion part inclined in a forward or reverse direction for a longitudinal direction of the extension part toward a leading portion of the extension part.

8. The micro needle according to claim 1, wherein the protrusion part has a width of 5 micrometer~5 millimeter, a space of 5 micrometer~5 millimeter, and a height of 5 micrometer~5 millimeter.

9. The micro needle according to claim 1, wherein the protrusion part has a width of 50 micrometer~1 millimeter, a shape of 50 micrometer~1 millimeter, and a height of 50 micrometer 1 millimeter.

10. The method according to claim 1, wherein the main body part comprises a connection means to connect the main body part to the medical device.

11. The micro needle according to claim 1, wherein the micro needle is capable of being connected or separated to or from the medical device by inserting the main body part into a recess formed in the medical device or extracting the main body part from the recess after the insertion.

12. The micro needle according to claim 1, wherein the main body part comprises at least a recess to connect the main body part to the medical device.

13. The micro needle according to claim 1, wherein the extension part has a length between 1.5 millimeter and 16 millimeter.

14. The micro needle according to claim 1, wherein the extension part has a length between 2 millimeter and 10 millimeter.

15. The micro needle according to claim 1, wherein the width and the length of the main body part is respectively within a range between 100 micrometer and 50 millimeter, and the thickness of the main body part is within a range between 100 micrometer and 10 millimeter.

16. The micro needle according to claim 1, wherein the width and the length of the main body part is respectively within a range between 500 micrometer and 5 millimeter, and the thickness of the main body part is within a range between 200 micrometer and 2 millimeter.

17. The micro needle according to claim 1, wherein the protrusion part is not formed on the outer side surface of the extension parts on the left part and the extension part on the right part.

18. A barb-wired micro needle monolithically formed from a single crystalline silicon comprising:
   a main body part capable of being insertion-mounted to a medical device and inserted into the body along with said medical device for picking a tissue sample from an organ in a body, the main body part including a medicine storage formed on a portion of one surface thereof and having a recess shape for storing medicine and a fluid passage formed therein to communicate with the medicine storage and made of single crystalline silicon;
   plural extension parts integrally extending from a side surface of the main body part, provided with the fluid passage therein and capable of being inserted into a biopsy tissue; and
   plural protrusion part integrally protruding from a side surface or both side surface of the extension parts which are opposite to each other, and capable of picking the biopsy tissue,
   wherein plural outflow ports of the fluid passage are formed on both side surfaces of each of the extension parts for injecting medicine into an organ in a body.

19. A barb-wired micro needle monolithically formed from a single crystalline silicon comprising:
   a main body part capable of being insertion-mounted to a medical device and inserted into the body along with said medical device for picking a tissue sample from an organ in a body, the main body part including a medicine storage formed on a portion of one surface thereof and having a recess shape for storing medicine and a fluid passage formed therein to communicate with the medicine storage and made of single crystalline silicon;
   plural extension parts integrally extending from a side surface of the main body part, provided with the fluid passage therein and capable of being inserted into a biopsy tissue; and
   plural protrusion parts integrally protruding from a side surface or both side surfaces of the extension parts which are opposite to each other, and capable of picking the biopsy tissue,
   wherein plural outflow ports of the fluid passage are formed on both side surfaces of each of the extension parts for injecting medicine into an organ in a body, and
   wherein at least two pairs of extension parts are integrally extended from upper and lower parts of one side of the main body part, wherein a pair of extension parts consists of two extension parts, one of which is extended from a left part of the one side of the main body part, and the other of which is extended from a right part of the one side of the main body part.

* * * * *